United States Patent [19]

LeClerc et al.

[11] Patent Number: 4,897,412
[45] Date of Patent: Jan. 30, 1990

[54] IMIDAZOLINES USEFUL IN LOWERING INTRAOCULAR PRESSURE

[75] Inventors: Gerard LeClerc, Grenoble, France; Didier Huber, Fort Worth, Tex.; Jacques Himber, Guebwiller; Guy Andermann, Strasbourg, both of France

[73] Assignee: Laboratories Alcon S.A., Kaysersberg, France

[21] Appl. No.: 299,273

[22] Filed: Jan. 19, 1989

Related U.S. Application Data

[60] Division of Ser. No. 154,267, Feb. 10, 1988, Pat. No. 4,801,617, which is a continuation-in-part of Ser. No. 35,119, Apr. 6, 1987, abandoned.

[51] Int. Cl.$^4$ .................. A61K 31/415; C07D 233/22
[52] U.S. Cl. ...................................... 514/401; 548/353
[58] Field of Search ......................... 548/353; 514/401

[56] References Cited

U.S. PATENT DOCUMENTS

| | | | |
|---|---|---|---|
| 4,195,085 | 3/1980 | Stone | 514/236.2 |
| 4,342,783 | 8/1982 | Morselli et al. | 514/652 |
| 4,444,782 | 4/1984 | DeMarinis et al. | 548/315 X |
| 4,450,170 | 5/1984 | Beeley et al. | 548/315 |
| 4,461,904 | 7/1984 | York, Jr. | 548/315 |
| 4,515,800 | 5/1985 | Carero et al. | 514/392 |
| 4,517,199 | 5/1985 | York, Jr. | 514/392 |

FOREIGN PATENT DOCUMENTS 155329  11/1968  Hungary .

OTHER PUBLICATIONS

McGuinness et al., "Timolol and Dipivalyl Epinephrine Combination Therapy", *Aus. J. of Oph.* 10, pp. 179–182 (1982).

Weinreb et al., "Effect of Adding Betaxolol to Dipivefrin Therapy", *Am J. of Oph.*, vol. 101, pp. 196–198 (1986).

LeClerc et al., "Agents Alpha-Adrénergiques Alcoylants", *Eur. J. Med. Chem.*, 13, No. 6, pp. 521–526 (1978).

LeClerc et al., "Unusual Reaction of N-Hydroxyphthalimido Ethers Leading to Oxygen-Nitrogen Heterocycles", *J. Org. Chem.* 47, pp. 517–523 (1982).

Ehrhardt, J. D., "Métabolisme du catapressan Action hypotensive du 4-hydroxycatapressan", *Therapie* XXVII, pp. 947–954 (1972).

Barefield et al., "Synthesis and Stereochemistry of Cobalt (III) Complexes of 1,3-Diamino-2-Propanol and Related Ligands", *Inorg. Chem.*, vol. 13, pp. 2611–2617 (1974).

*Chem. Abstracts*, 70 106522g (1969)[Hungary 155,329, 11/22/88].

LeClerc et al., "Synthéses et réactivité de la p-aminoclonidine" *Bulletin de la Societe Chimique de France*, No. 9–10, pp. II-520–528 (1979).

*Primary Examiner*—Richard A. Schwartz
*Attorney, Agent, or Firm*—James A. Arno; Gregg C. Brown

[57] ABSTRACT

Antiglaucoma compounds having beta adrenoreceptor antagonist properties and alpha adrenoreceptor antagonist properties are described. The compounds comprise a beta blocker-derived moiety designed to provide beta antagonist properties and an imidazolidine moiety designed to provide alpha-antagonist properties. Methods of synthesizing the compounds are also described. The compounds are useful in the treatment of glaucoma due to their ability to lower elevated intraocular pressure.

3 Claims, 1 Drawing Sheet

IMIDAZOLINES USEFUL IN LOWERING INTRAOCULAR PRESSURE

CROSS REFERENCE TO RELATED APPLICATION

The present application is a division of U.S. patent application Ser. No. 154,267 filed Feb. 10, 1988 now U.S. Pat. No. 4,801,617 which is a continuation in-part of U.S. application Ser. No. 035,119 filed Apr. 6, 1987 now abandoned.

BACKGROUND OF THE INVENTION

The present invention relates to new chemical compounds useful in the treatment of glaucoma and other conditions involving elevated intraocular pressure, processes for synthesizing the compounds, pharmaceutical compositions containing the compounds, and methods of treating glaucoma and other conditions involving elevated intraocular pressure with the present compositions.

Compounds having beta-antagonistic properties are also referred to as "beta-adrenoreceptor antagonists" or, more commonly "beta blockers". Some types of beta blockers are known to be effective in lowering intraocular pressure, primarily by decreasing aqueous humor formation. Compounds having alpha-antagonistic properties are commonly referred to as "alpha-antagonists". These compounds are also known to be effective in lowering intraocular pressure.

The use of two or more different types of drugs to lower elevated intraocular pressure has been a common practice, particularly in connection with patients who exhibit severe elevations in intraocular pressure and/or develop a resistance to the intraocular pressure lowering effect of a single drug. This practice has included combination therapy with a beta blocker and an alpha agonist. Reference is made to the following articles for further background in this regard: McGuinness et al., "Timolol and Dipivalyl Epinephrine Combination Therapy", *Aust. J. Ophthalmol.*, Vol. 10, pages 179–182 (1982); and Weineb et al, "Effect of Adding Betaxolol to Dipivefrin Therapy", *Am. J. Ophthalmol.*, Vol. 101, pages 196–198 (1986).

SUMMARY OF THE INVENTION

The present invention is directed to the provision of new compounds (i.e., molecules) which have both beta blocking and alpha antagonist activity. With this approach, it is believed that problems inherent to the prior practice of administering two or more drugs to a glaucoma patient will be avoided, as will be the compatibility problems which may be associated with combining two or more compounds in a single composition. The compounding of side effects which may be experienced with both of these conventional approaches to combination therapy may also be avoided.

The compounds of the present invention have been designed to comprise two different pharmacological properties: antagonism of betaadrenoreceptors and antagonism of alpha adrenoreceptors. The compounds are derived from an associative synthesis involving a beta adrenergic antagonist moiety (i.e., a beta blocker) and an imidazolidine moiety. Representative compounds of the present invention have been shown to lower intraocular pressure.

DETAILED DESCRIPTION OF THE INVENTION

Figure 1:
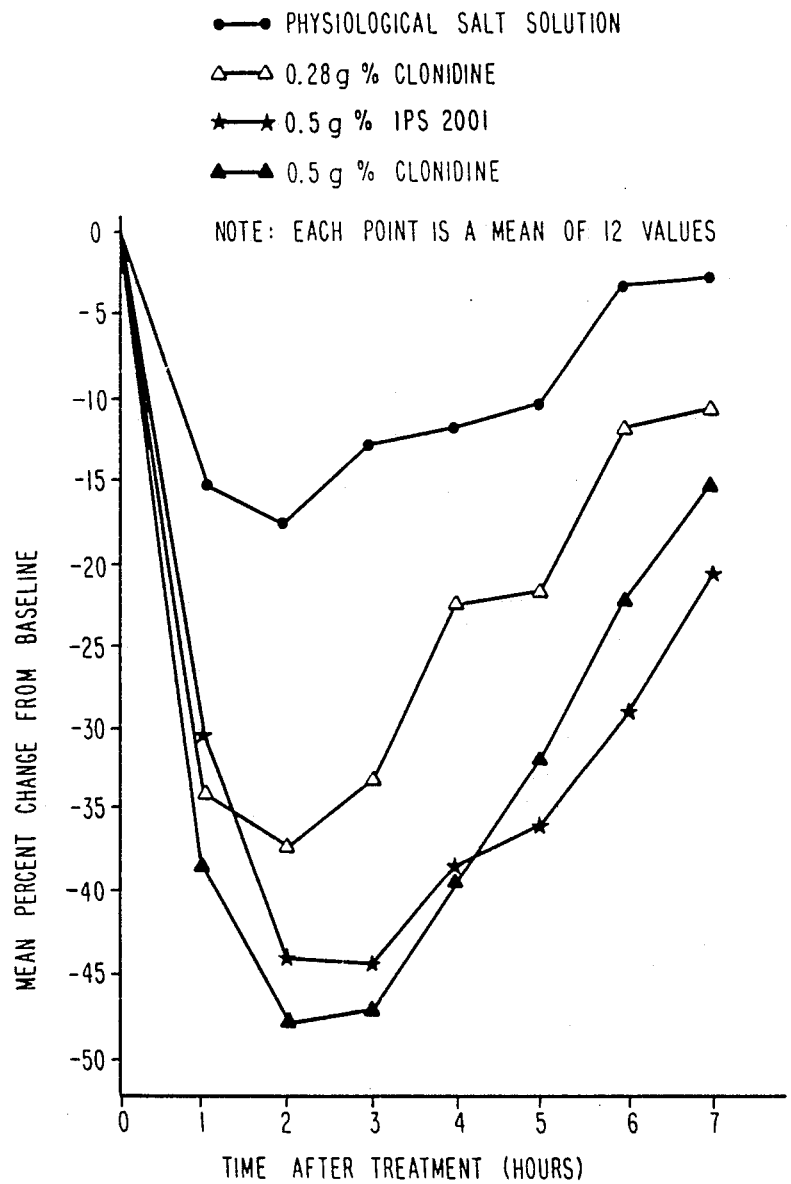
FIG. 1, the sole figure of drawing, is a graphic illustration of the data discussed in connection with Example 6.

The following compounds of the present invention are selected from compounds having the following Structures (I)–(V):

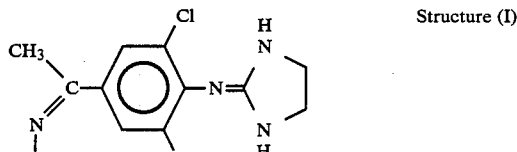
Structure (I)

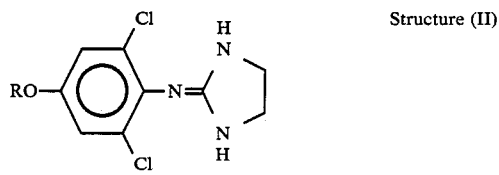
Structure (II)

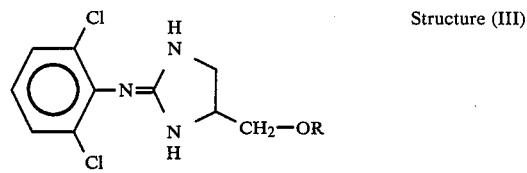
Structure (III)

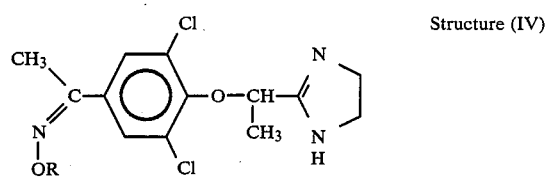
Structure (IV)

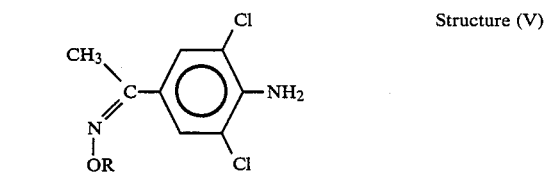
Structure (V)

wherein R is

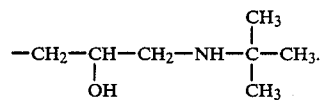

The compounds of Structures (I)–(V) may be synthesized according to the reaction schemes described below.

EXAMPLE 1

The compounds of Structures (I) may be prepared by reacting: (A) p-acetyl clonidine and (B) 1-aminooxy-2-hydroxy-3-tert-butylaminopropane. The synthesis of (A) is described by G. Leclerc et al. in *Bull. Soc. Chem. Fr.*, Vol. II, Page 520 (1979). The synthesis of (B) is described by G. Leclerc et al. in the *Journal of Organic Chemistry*, Vol. 47, page 517 (1982). The entire contents of these two publications by Leclerc et al. are incorporated herein by reference. The overall reaction scheme may be illustrated as follows:

of water. The organic layer was dried and evaporated. The crude sample (3.2 g) was separated on a silica gel column using a EtOAc/MeOH/Et$_3$N : 90:5:5 system as

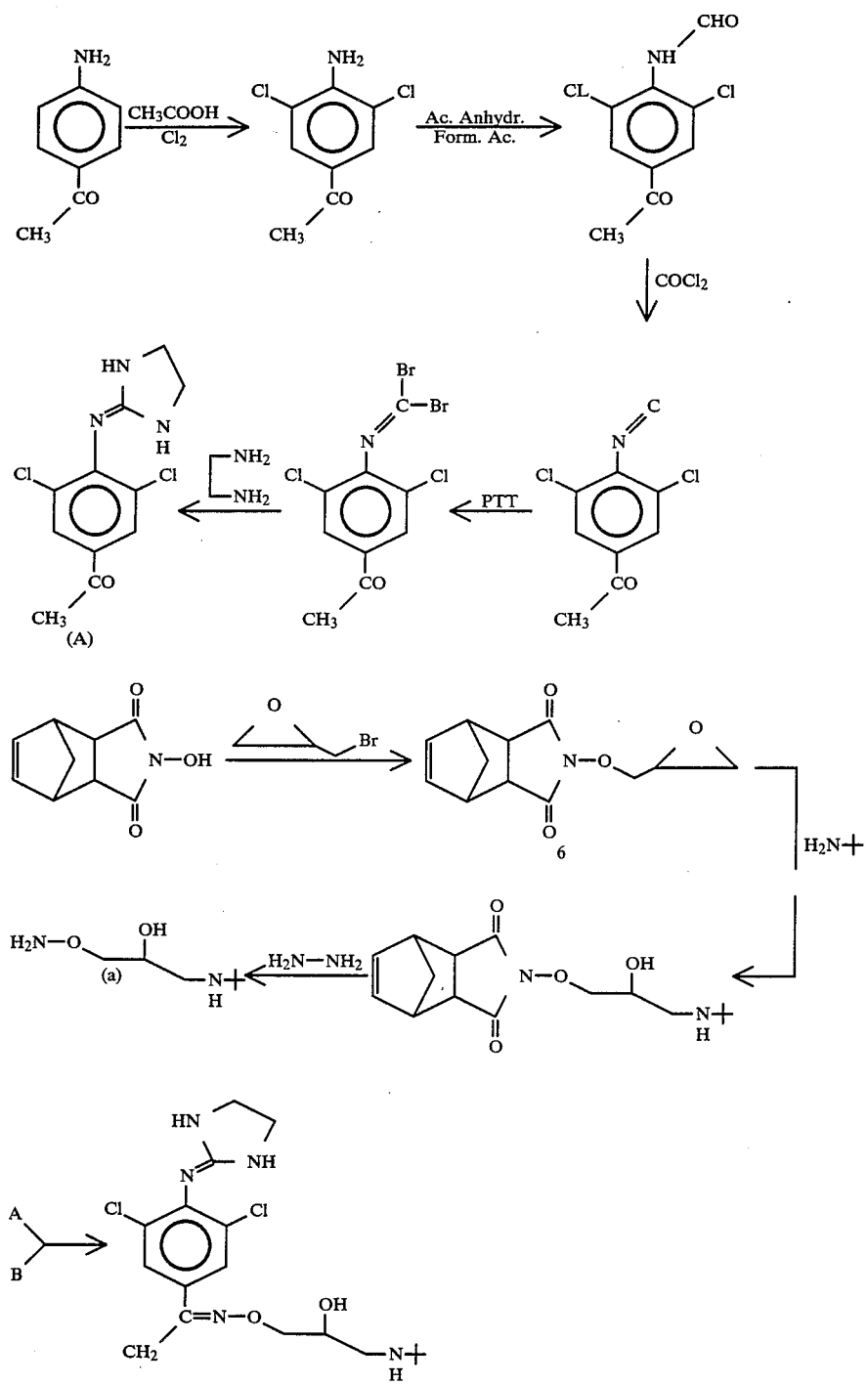

solvent. 2.62 g (yield 63%) of the compound of Structure (I) were obtained.

In accordance with the above-described reaction scheme, 2.72 g (10 mmol) of p-acetyl clonidine and 1.62 g (10 mmol) of 1-aminooxy-2-hydroxy-3-tert-butylaminopropane in 200 ml of ethanol were refluxed for 24 hours. After evaporation, the residue was dissolved in 100 ml of EtOAc and washed with 3×50 ml

EXAMPLE 2

The compound of Structure (II) may be prepared according to the following reaction scheme:

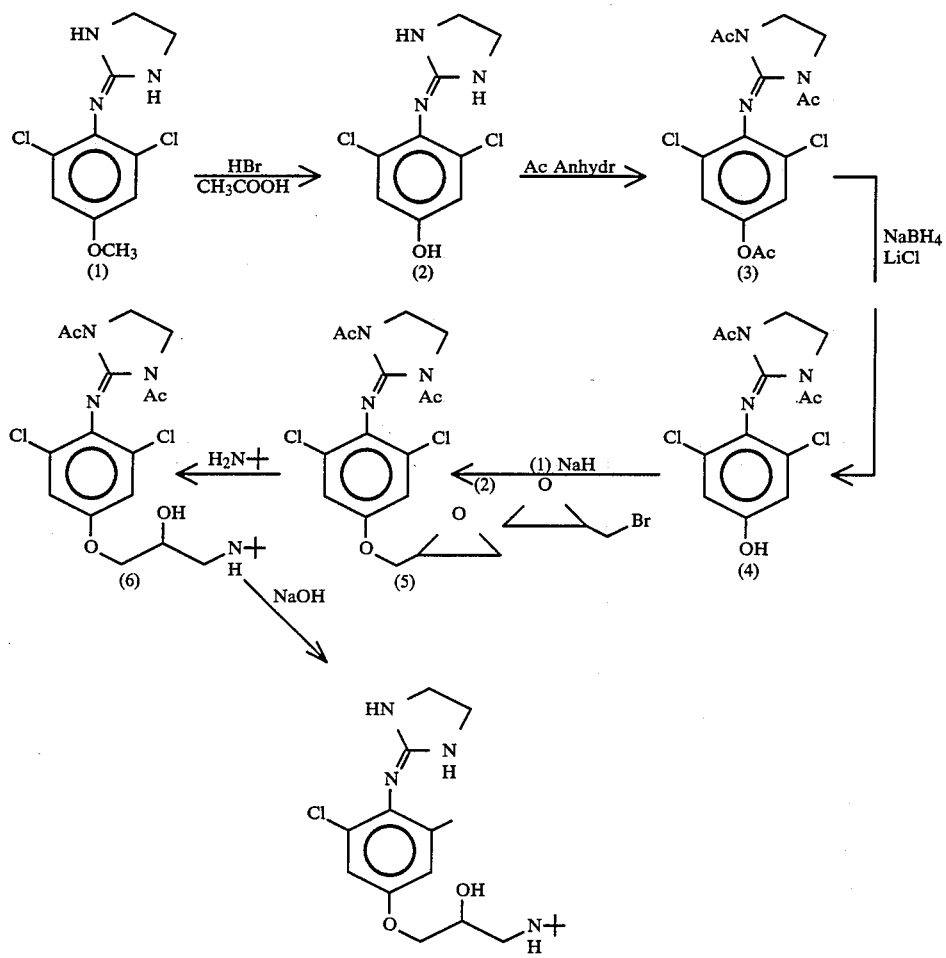

The synthesis of (2) is described by J. Ehrhardt in *Therapie.* pages 947–954 (1972).

To synthesize (3), 5 g (20.3 mmol) of p-hydroxyclonidine were refluxed in 50 ml of acetic anhydride during one night. After evaporation of the solvent, the crude sample (5.5 g) was separated on a silica gel column using EtOAc as solvent. 4.8 g (yield 63%) of the intermediate (3) were obtained.

To synthesize (4), a mixture of 756.6 mg of $NaBH_4$ (20 mmol) and 848 mg of LiCl (20 mmol) was stirred for 2 hours in 50 ml of diglyme. Then 7.44 g (20 mmol) of the triacetylated clonidine were added. The mixture was stirred at 50 C. for 18 hours. After hydrolysis with 70 ml of water the solution was extracted with 3×50 ml of EtOAc. After drying the organic layer on $MgSO_4$, the solvent was evaporated. The crude sample was separated on a silica gel column using $EtOAc/MeOH/Et_3N$ 65/25/10 as solvent. 5.2 of diacetylated clonidine (yield 70%) were obtained.

To synthesize (5) and (6), 5 g of diacetylated clonidine (4) (15 mmol) was dissolved in 50 ml of DMF and 360 mg of NaH (15 mmol) were added. After 2 hours at room temperature, 1.3 ml of epibromo-pydrin were added. The mixture was stirred over night. Then, the DMF was evaporated and the residue dissolved in 50 ml of absolute methanol. After 24 hours of reaction time, the solvent was evaporated and the crude sample separated on a silica gel column using EtOAc/MeOH-/$Et_3N$: 90/5/5 as solvent. 3.8 g of the intermediate (6) (yield 55%) were obtained.

To complete the synthesis, 3.5 g of the diacetylated clonidine (6) were dissolved in 20 ml of THF and 20 ml of NaOH (0.5N). The mixture was refluxed for 6 hours. The THF was then evaporated and the aqueous layer adjusted to pH 7 and extracted with EtOAc. The organic layer was dried over $MgSO_4$ and evaporated. After separation on a silica gel column using EtOAC/-MeOH/$Et_3N$:90/5/5 as solvent, 2.2 g of the compound of Structure (II) were obtained.

The synthesis utilized to prepare the compound of Structure (III) represents a novel aspect of the present invention. It was believed initially that the only feasible approach to produce this compound would be by selective alkylation of an alcohol function in the presence of a 2-imino-imidazolidine. For this type of reaction, the imino-2-imidazolidine group had to be protected. Prior to the present invention, the most satisfactory technique was to transform the guanidine into its N-acetylated form. Our first attempt was to transform (1) into (2) by a selective O-deacetylation. However, as outlined in Scheme A below, treating the diacetylated compound (2) with NaH in DMF gave (3), with a 40% yield, via an N→O acetyl transfer. The structure of (3) was confirmed by the appearance of a methyl ester singlet at 2.2 ppm and the disappearance of an N-acetyl singlet at 2.7 ppm, in the NMR spectrum. A similar migration has been described previously among acetylated aminoalcohols.

the tetrahydropyranyl-protecting group in 2N HCl/EtOH. Sequential treatment of (9) with EtONa

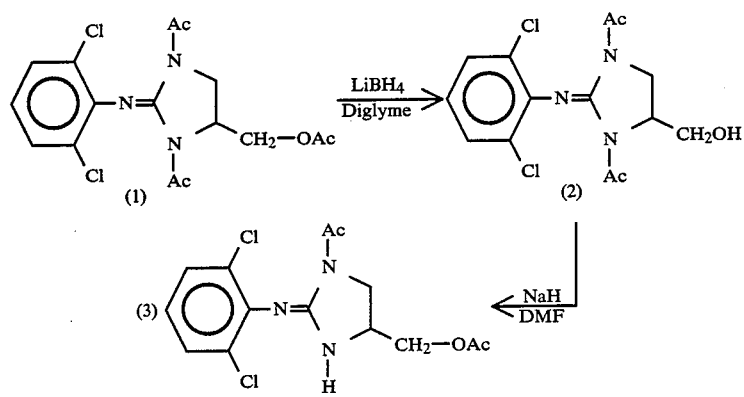

To avoid this type of reaction, a protective group which is stable under basic conditions is employed in the synthesis method of the present invention. The use of a 3,4-dimethoxybenzyl derivative to protect a pyrrole —NH group, cleaved under acid conditions, has recently been advocated. The synthesis method of the present invention employs a 3,4-dimethoxybenzyl as a guanidine protective group.

The reaction scheme is set forth in Example 3 below. The tetrahydropyranyl (4) is synthesized from 2,3-dibromopropanolol, as described by E. Barefield et al. in *Inorganic Chemistry*, Vol. 14, page 11 (1974). Condensation of the diamino compound (4) with 3,4 dimethoxybenzaldehyde in refluxing toluene gives the di-imine (5), which is then reduced by catalytic hydrogenation (PtO$_2$ in ethanol) to the N,N'-di-(3,4-dimethoxybenzyl) ethylenediamine derivative (6). The dichloroisocyanide (7) is obtained from 2,6-dichloro aniline by formylation with a formic-acetic anhydride mixture followed by treatment with thionyl chloride and sulfuryl chloride, as described in Hungarian Patent No. 155,329, as well as *Chem. Abstracts*, 70, 106,522 (1969).

Treatment of (7) with the protected aminoalcholol (6) provides an excellent yield of the 2-imino-imidazolidine (8) which is transformed into alcohol (9) by removal of (1.1 equiv.), epibromohydrine in DMF (1.1 equiv.) and t-butylamine in ethanol (3.3 equiv.), which treatment is designated as "a, b, c" in the schematic reaction diagram below, gives (10). The 3,4-dimethoxybenzyl blocking groups (designated as "Ar" in the reaction scheme) are cleaved in a mixture of CF$_3$COOH, H$_2$SO$_4$ and anisole to provide (11), referred to above as the compound of Structure (III).

The interest in using the 3,4-dimethoxybenzyl unit as a "blocking group", removable under acidic conditions, for 2-iminoimidazolidine derivatives is an extension of the observation that cleavage of an N-benzyl group through catalytic hydrogenation (Pd/C) provokes, at least partially, hydrogenolysis of the Ar-Cl bonds. Also, the use of the N-acetylated derivative gave rise to acetyl transfer, as shown in Scheme A above. It is believed that the results achieved with the present synthesis method show, for the first time, that the 3,4-dimethoxybenzyl group can be used as a protective group for 2-iminoimidazolidine derivatives. The above-described synthesis is further illustrated in the following example.

EXAMPLE 3

Structure (III) may be prepared according to the following reaction scheme:

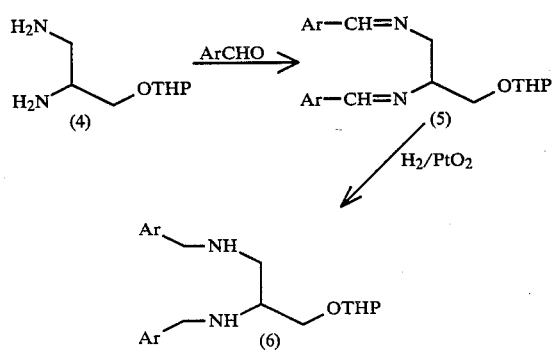

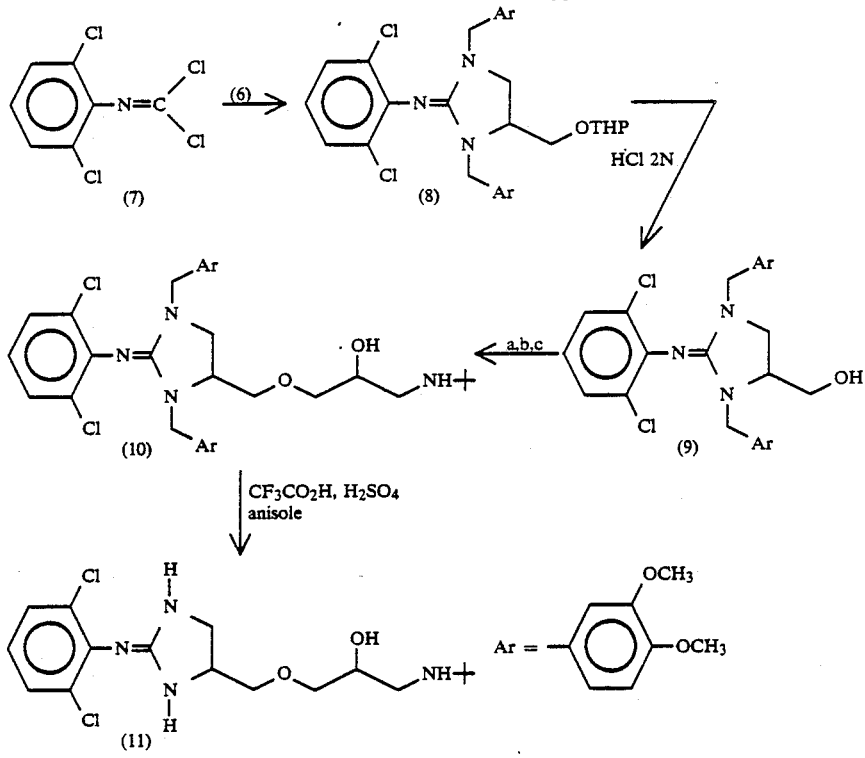

The reaction may be conducted according to the following steps:

(A) 2,3 bis-(3,4-dimethoxybenzylamino)-1-(2-tetrahydropyranyl) propanol (5).

A solution of 2,3-diamino-1-(2-tetrahydropyranyl) propanol (32 g, 0.184 mol) and 3,4-dimethoxybenzaldehyde (61.15 g, 0.368 mol) in 300 ml of toluen was heated under reflux for 18 hours. The solvent was evaporated and the crude mixture (83 g) was used without further purification for the next step.

(B) 2.3 bis-(3,4-dimethoxybenzylamino)-1-(2 tetrahydropyranyl) propanol (6).

A solution of 83 g of (5) in 200 ml of absolute ethanol, containing 0.3 g of $PtO_2$ was hydrogenated at atmospheric pressure and room temperature. After 24 hours, the catalyst was filtered off and the solvent evaporated. The crude product was chromatographed on a silica gel column with $EtOAc-Et_3N-MeOH$ (90:5:5) to give diamine (6) (41.5 g) with a 47.6% yield from (4).

(C) 2-(2,6-dichlorophenylimino)-1,3 bis-(3,4 dimethoxy-benzyl)-4-(2-tetrahydropyranyl-oxy-methyl)imidazolidine (8).

14.9 g (61.4 mmol in 15 ml of EtOAc) of (7) and 29.1 g (61.4 mmol) of (6) (in 12 ml EtOAc) were added dropwise simultaneously to a solution of 24 ml of $Et_3N$ in 34 ml of EtOAc at room temperature. The mixture was stirred overnight. The solution was filtered and extracted 3 times with 50 ml of water. The organic layer was dried with $MgSO_4$ and the solvent evaporated. The crude mixture (26 g) was chromatographed on a silica gel column with EtOAc/Hexane (60:40) to give compound (8) (14.2 g) with a 36% yield.

(D) 2-(2,6-dichlorophenylimino)-1,3 bis-(3,4 dimethoxybenzyl)-4-hydroxymethyl imidazolidine (9).

9.66 g (15 mmol) of (8) were treated for 6 hours with 30 ml of 2N HCl/EtOH solution (5:5). After extraction with EtOAc, 7.2 g of crude sample were obtained. After silica gel column separation, using EtOAc/Hexane (6:4) as solvent, 6.3 g of (9) (75% yield) were obtained.

(E) 2-(2,6-dichlorophenylimino)-1,3 bis-(3,4 dimethoxybenzyl)-4-(3-tert-butylamino-2-hydroxy propanoxymethyl)imidazolidine (10).

0.13 g of Na were dissolved in 20 ml of methanol. After dissolution, 2.8 g of (9) (0.5 mol) in 10 ml of methanol were added. The mixture was refluxed for one hour. Then the solvent was evaporated. The residue was dissolved in 40 ml of DMF and 0.48 ml (5.6 mmol) of epibromohydrin were added. The mixture was stirred for 18 hours at room temperature, after which time the DMF was evaporated. The crude mixture was dissolved in 30 ml of ethanol and 1.1 g (15 mmol) of tert-butylamine were added. After evaporation of the solvent and EtOAc/water extraction, the organic layer was dried over $MgSO_4$ and filtered. Concentration gave 3.2 g of crude product which was separated over a silica gel column using $EtOAc/MeOH/ET_3N$: (8:1:1) as solvent. After purification, 2.1 g of (10) were obtained (yield 61%).

(F) 2-(2,6-dichlorophenylimino)-4-(3-tert-butylamine-2-hydroxy propanoxymethyl)imidazolidine (11).

To a solution of 10 ml of $CF_3COOH$, 2.5 ml of concentrated $H_2SO_4$ and 3.4 ml of anisole were added 1.8 g (2.6 mmol) of (10) dissolved in 3 ml of $CF_3COOH$. The resulting solution was stirred for 2 hours. After that time, the trifluoroacetic acid was evaporated, and 20 ml of water was added to the residue. The mixture was alkalanized with $KHCO_3$ and extracted with EtOAc. After separation on a silica gel column, 0.77 g of (11) were obtained (yield 76%).

EXAMPLE 4

The compound of Structure (IV) may be prepared according to the following reaction scheme:

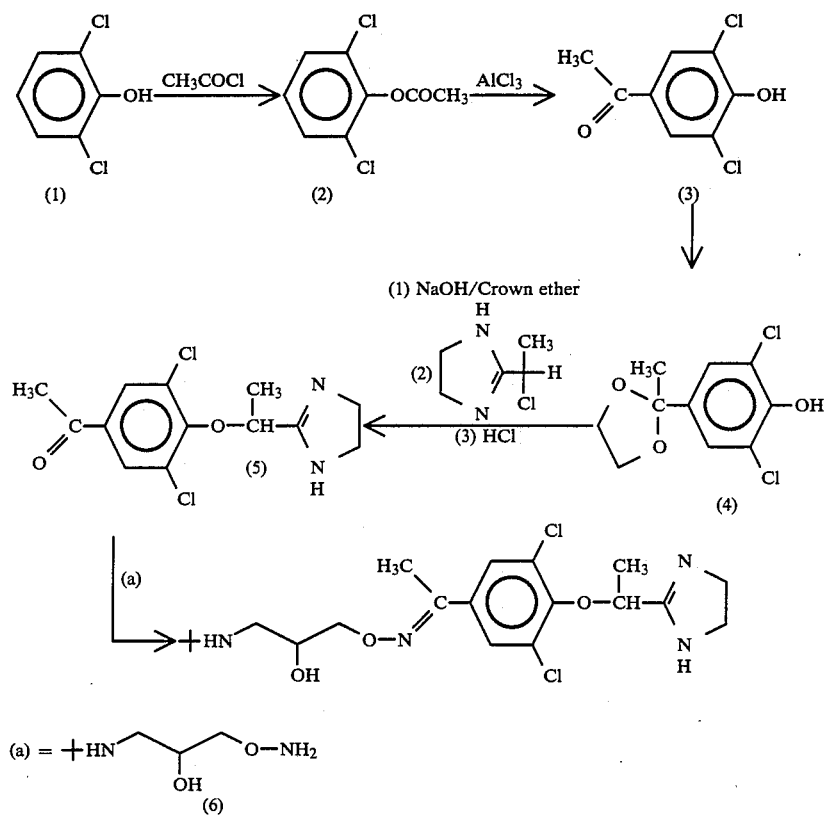

The synthesis of starting materials (1)-(3) is known in the art. To prepare the next intermediate, (4), 9 g (44 mmol) of (3), 20 ml of ethylene glycol, 100 ml of benzene and 3 mg of p-toluene sulfonic acid were refluxed overnight with a Dean-Stark. After evaporation of the solvent and separation on a silica gel column, 9.2 g of the cetal (4) were obtained.

To prepare the next intermediate, (5), 5 g of (4) (20 mmol) were dissolved in 140 ml of dioxanne. 960 mg of NaH were then added. After 2 hours, 2.65 g of 2,alpha-chloroethyl imidozoline (6), 10 mg of NaI and 4 ml of crown ether 15-5 were added. The mixture was refluxed for 18 hours. After evaporation of dioxanne, an EtOAc/water extraction (water:1N HCl solution) was conducted. Then the aqueous layer was alkalinized and extracated with EtOAc. After purification on a silica gel column using EtOAc/MeOH/Et₃N: 80/10/10 as solvent, 2.3 g of (5) was obtained.

To complete the synthesis, 3 g of p-acetyl lofexidine (5) (10 mmol) and 1.62 g of oxyamine (6) were dissolved in 120 ml of ethanol and refluxed for 18 hours. After separation on a silica gel column using EtOAc/MeOH/NEt3:70/20/10 as solvent, 2.1 g of the compound of Structure (IV) were obtained (yield 47%).

EXAMPLE 5

The compound of Structure (V) may be prepared according to the following reaction scheme:

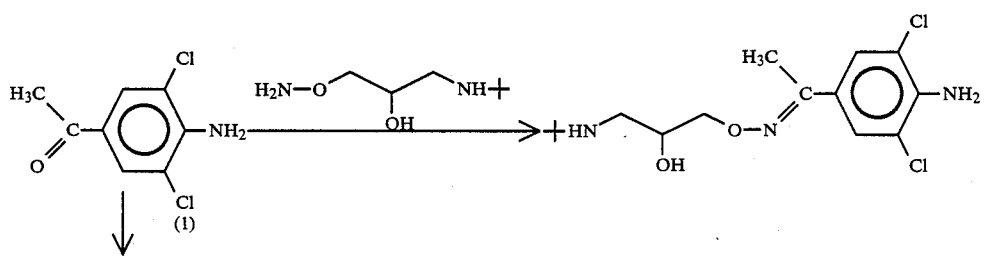

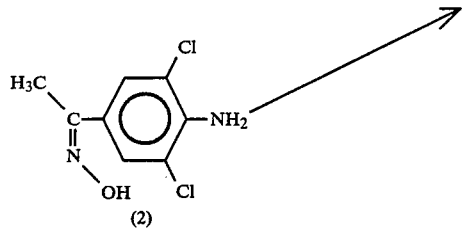

(2)

The starting material (1) is obtained as described in Example 1 above. To prepare (2), 2.04 g of p-acetyl aniline (10 mmol) and 1.12 g of hydroxyamine were mixed in 10 ml of ethanol and 10 ml of water containing 2 g of NaOH. The solution was refluxed for 10 hours. The ethanol was evaporated and the aqueous layer was extracted with ether after being acidified to pH 3-4. The organic layer was dried over MgSO₄ and evaporated. 1.87 g of (2) were obtained (yield 85%).

To complete the synthesis, 1.5 g of (2) (6.85 mmol) in 30 ml of DMF were treated with 330 mg of NaH for 2 hours. Then, 0.6 ml of epibromohydrin in 20 ml of DMF were added. The mixture was stirred at room temperature for 12 hours. DMF was evaporated and the residue was dissolved in 40 ml of ethanol and treated with 2.2 ml of tert-butyl amine. After 12 hours, the solvent was evaporated and the crude sample separated on a silica gel column using EtOAc/MeOH/Et₃N: 90/5/5 as solvent. 930 mg of the compound of Structure (V) were obtained (yield 39%).

Data relating to the IOP lowering activity of the compound of Structure (I) is set forth in the following example.

EXAMPLE 6

Twelve New Zealand Albino rabbits with alpha-chymotrypsin induced intraocular hypertension were used. IOP was measured using pneumatonometry before and at 1, 2, 3, 4, 5, 6 and 7 hours following a single instillation of 100 microliters of the compound of Structure (I) at a concentration of 0.5%, or clonidine at 0.5% and 0.28%, or a saline solution, into the right glaucomatous eye. All experiments were carried out in a masked manner.

Surface anesthesia was determined with an esthesiometer by measuring the ability of topically applied drugs to abolish the palpebral reflex of the cornea of 6 New Zealand albino rabbits. Stimulations were carried out before and after instillation of 100 microliters of the test compounds (i.e., the compound of Structure (I) and clonidine) at a concentration of 0.5%, into the right eye and then monitored for 6 hours.

As shown in FIG. 1, clonidine and the compound of Structure (I) at a concentration of 0.5% (free base) produce a significant and similar reduction of IOP in the rabbit, with a maximum effect (decrease by 45%) at 2 and 3 hours after instillation.

In order to evaluate the gain in decrease of IOP obtained with the compound of Structure (I), the effect of clonidine at a concentration of 0.28% (free base) was tested. This concentration represents the quantity of clonidine included in the present compound at a concentration of 0.5%. The data presented in FIG. 1 show that the present compound is more potent in reducing IOP at a concentration of 0.5% than clonidine at a concentration of 0.28%. These results suggest that the clonidine structure included in the present compound is not solely responsible for the significant IOP-lowering action of the compound. A synergistic effect between the beta-blocker and imidazolidine moieties may explain the efficacy of the compound of Structure (I). The compound of Structure (I) did not produce evident ocular irritation or toxicity on the rabbit eye. No surface anesthesia was observed on the rabbit cornea. Also, no systemic cardiovascular side-effects (i.e., blood pressure and heart rate) have been observed as a response to topical administration.

As will be appreciated by those skilled in the pharmaceutical arts, the compounds of Structures (I)-(V) may be contained in various types of pharmaceutically acceptable dosage forms suitable for topical delivery of the compounds to the eye. The compounds will typically be contained in aqueous formulations, such as aqueous eye drop solutions, and may contain various adjuvant ingredients such as buffering agents, disinfectants, surfactants and preservatives.

The compounds of Structures (I)-(V) may be utilized to treat glaucoma and to treat elevated intraocular pressure associated with other disease states. The dosages utilized and the frequency of dosage will vary depending on factors such as the nature and severity of the condition being treated. The establishment of dosage regimens is within the skill of the clinician. In general, the compounds will be applied topically to the eye in an amount effective to cause a therapeutic reduction in intraocular pressure, and at a frequency to maintain that reduction.

What is claimed is:

1. A compound formula:

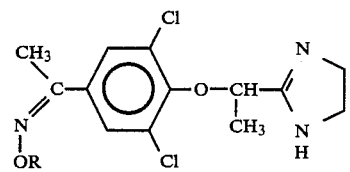

wherein R is

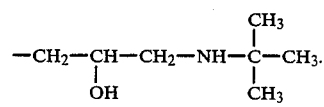

2. A topical ophthalmic composition useful in the treatment of elevated intraocular pressure, comprising an effective amount of a compound of formula:

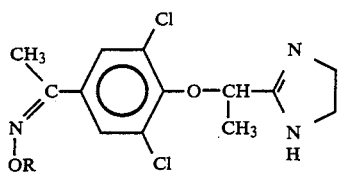
wherein R is
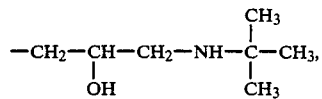
and a pharmaceutically acceptable carrier therefor.
3. A method of lowering intraocular pressure which comprises applying an ophthalmic composition according to claim 2 topically to the affected eye.
* * * * *